United States Patent
Williams

(10) Patent No.: US 11,685,733 B2
(45) Date of Patent: Jun. 27, 2023

(54) COMPOUNDS FOR TREATING RAC-GTPASE MEDIATED DISORDER

(71) Applicant: Children's Medical Center Corporation, Boston, MA (US)

(72) Inventor: David A Williams, Dover, MA (US)

(73) Assignee: Children's Medical Center Corporation, Boston, MA (US)

( * ) Notice: Subject to any disclaimer, the term of this patent is extended or adjusted under 35 U.S.C. 154(b) by 129 days.

(21) Appl. No.: 16/962,724

(22) PCT Filed: Jan. 17, 2019

(86) PCT No.: PCT/US2019/014035
§ 371 (c)(1),
(2) Date: Jul. 16, 2020

(87) PCT Pub. No.: WO2019/143833
PCT Pub. Date: Jul. 25, 2019

(65) Prior Publication Data
US 2020/0347044 A1    Nov. 5, 2020

Related U.S. Application Data

(60) Provisional application No. 62/619,455, filed on Jan. 19, 2018.

(51) Int. Cl.
*C07D 413/14* (2006.01)
*A61P 35/02* (2006.01)
*A61K 9/00* (2006.01)

(52) U.S. Cl.
CPC ............ *C07D 413/14* (2013.01); *A61P 35/02* (2018.01); *A61K 9/0019* (2013.01)

(58) Field of Classification Search
CPC ................................ C07D 413/14; A61P 35/02
See application file for complete search history.

(56) References Cited

U.S. PATENT DOCUMENTS

2010/0035919 A1   2/2010  Vasudevan et al.
2015/0265608 A1   9/2015  Williams

OTHER PUBLICATIONS

EP Extended European Search Report in EP Appln. No. 19741188.7, dated Feb. 22, 2021, 5 pages.
PCT International Preliminary Report on Patentability in International Appln. No. PCT/US2019/014035, dated Jul. 21, 2020, 7 pages.
PCT International Search Report and Written Opinion in International Appln. No. PCT/US2019/014035, dated May 23, 2019, 15 pages.
Pubchem AID 2031, "Oxadiazole SAR compounds tested via Multiplex dose response to identify 1-3 specific small molecule inhibitors of Ras and Ras-related GTPases specifically Rab7 wildtype," May 6, 2019, 16 pages.
Pubchem CID 28071126, Compound Summary, May 28, 2009, 13 pages.
Cancelas et al., "Rac GTPases differentially integrate signals regulating hematopoietic stem cell localization," Nature Medicine, Aug. 2005, 11(8):886-91.
Nunes et al., "Validation of a small molecule inhibitor of PDE6D-RAS interaction with favorable anti-leukemic effects," Blood Cancer Journal, Apr. 14, 2022, 12(4), 14 pages.
Thomas et al., "Rac guanosine triphosphatases represent integrating molecular therapeutic targets for BCR-ABL-induced myeloproliferative disease," Cancer Cell, Nov. 13, 2007, 12(5):467-78.

*Primary Examiner* — Samira J Jean-Louis
(74) *Attorney, Agent, or Firm* — Fish & Richardson P.C.

(57) ABSTRACT

This disclosure relates to certain compounds that are effective in the treatment of a Rac-GTPase mediated disorder (e.g., acute lymphoblastic or chronic myelogenous leukemia), as well as methods for the manufacture of and the use of these compounds (e.g., for treating a Rac-GTPase mediated disorder).

12 Claims, 7 Drawing Sheets

COMPOUNDS FOR TREATING RAC-GTPASE MEDIATED DISORDER

CROSS-REFERENCE TO RELATED APPLICATIONS

This application is a 371 national stage entry of PCT/US2019/014035, filed on Jan. 17, 2019, which claims priority under 35 U.S.C. § 119(e) to U.S. Provisional Application No. 62/619,455, filed Jan. 19, 2018. The disclosures of the parent applications are incorporated herein in their entirety.

BACKGROUND

Rho GTPases comprise a branch of the Ras superfamily of small GTPases. They play a key role in the modulation of a wide array of cellular processes including cell migration, cell polarization, membrane trafficking, cytoskeleton arrangements, proliferation, apoptosis, and transcriptional regulation. (Etienne-Manneville, S. et al (2002). Nature 420, 629-635.; Boettner, B. et al. (2002). Gene 286, 155-174.) Hence, Rho GTPases have been implicated in the pathogenesis of various human diseases including cardiovascular diseases and cancer (Hall, A. Science 1998, 279, 509-514; Wennerberg, K., and Der, C. J. (2004) J. Cell Sci. 117, 1301-1312.; Ridley, A. J. (2006) Trends Cell Biol. 16, 522-529).

The Rho family is comprised of 22 genes encoding at least 25 proteins in humans including Rac. Rho family members bind GTP and transition between an inactive GDP-bound and an active GTP-bound state. In doing so, many of the Rho family members exhibit a GTPase activity when in their active state. This cycling between states is regulated by: guanine nucleotide exchange factors (GEFs); the GTPase activating proteins (GAPs); and GDP dissociation inhibitors (GDIs) which act as negative regulators. (Malumbres, M. et al (2003) Nat. Rev. Cancer 3, 459-465). In quiescent cells, Rho GTPases are predominantly present in an inactive GDP bound state whereas upon growth stimulation, GEFs are activated and subsequently stimulate the guanine nucleotide exchange activity to promote formation of the active GTP bound Rho. When bound to GTP, active Rho GTPases interact with downstream effectors including protein kinases and other proteins with adaptor functions. The intrinsic GTP hydrolysis functionality of Rho GTPases is later stimulated by the Rho specific GTPase activating protein. This returns the Rho protein to its inactive state. Rac-specific RhoGEFs include Tiam1 and Trio (Gao, Y. et al. (2004). Proc. Natl. Acad. Sci. USA 101, 7618-7623.)

The Rac subfamily has also been linked to cellular transformation and hence, the aberrant activity of Rho GTPases is associated with cancer. They play an essential role in transformation caused by Ras and other oncogenes. The Rac1b splice variant of Rac1 has been shown to be constitutively active and transforming; its overexpression has been observed in both breast and colon cancers (Qiu, R. G., et al. (1995) Nature 374, 457-459; Khosravi-Far, R., et al (1995) Mol. Cell. Biol. 15, 6443-6453; Renshaw, M. W. et al (1996) Curr. Biol. 6, 76-83; Ferraro, D., et al. (2006) Oncogene 25, 3689-3698). Rac3 mutants, for example, have been noted in brain tumors and both Rac1 and Rac3 have been linked to glioblastoma invasion (Hwang, S. L. et al (2005) J. Clin. Neurosci. 12, 571-574).

In malignant cells, aberrant Rho GTPase activity results from changes in the expression of Rho GTPases or the perturbed function of either GEFs or GAPs which regulate the function of Rho. (Karnoub, A. E. et al (2004). Breast Cancer Res. Treat. 84, 61-71.) Due to the evidence of Rho involvement in cell transformation, Rho GTPases are probable targets for anti-cancer therapies. Compounds that inhibit GEF interaction with their respective Rho family members would be useful inhibitors of Rho GTPase, such as Rac, and exhibit great specificity. To date, small molecule NSC23766 (i.e., N6-[2-[[4-(diethylamino)-1-methylbutyl]amino]-6-methyl-4-pyrimidinyl]-2-methyl-4,6-quinolinediamine trihydrochloride) has been identified as binding to Rac1 and preventing its activation by Rac-specific RhoGEFs. Some GEF activity, however, was not blocked.

Chronic myelogenous leukemia (CML) is a malignant disease characterized by expression of p210-BCR-ABL, the product of the Philadelphia chromosome. Also known as chronic granulocytic leukemia (CGL), it is a cancer of the white blood cells and is characterized by the increased and upregulated growth of mainly myeloid cells in the bone marrow and the accumulation of these cells in the blood. The deficiency of the Rho GTPases Rac1 and Rac2 in a murine model has shown a significant reduction of p210-BCR-ABL-mediated proliferation. Rac has also been shown to play a role in other types of leukemias such as MLL-mediated acute leukemia. (Mizukawa B. et al., Blood 2011; 118:5235-45). The above evidence has strongly suggested Rac as a potential target for leukemia therapy. (E K Thomas et al, Leukemia 22, 898-904, May 2008).

SUMMARY

This disclosure is based on the discovery of certain anticancer compounds identified through analysis of virtual docking onto the Rac-GTPase protein. In particular, one or more of these compounds identified by this assay unexpectedly exhibited superior activity in inhibiting proliferation of cancer cells with low toxicity to normal cells.

In one aspect, this disclosure features compounds of formula (I) or a salt thereof (e.g., a pharmaceutically acceptable salt thereof):

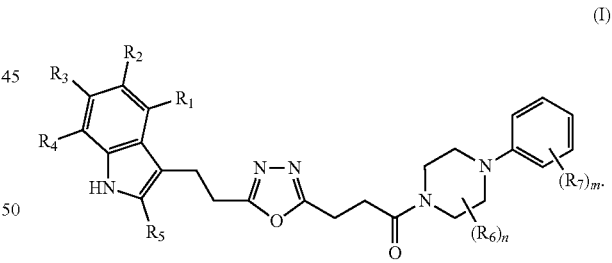

(I)

In formula (I), n is 0, 1, 2, 3, or 4; m is 0, 1, 2, 3, or 4; each of $R_1$, $R_2$, $R_3$, $R_4$, and $R_5$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$; each of $R_6$, independently, is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_aC(O)NR_aR_b$, $S(O)_2NR_aR_b$, or $NR_aR_b$; each of $R_7$, independently, is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, COOR$_a$, OC(O)R$_a$, C(O)R$_a$, C(O)NR$_a$R$_b$, S(O)$_2$NR$_a$R$_b$, or NR$_a$R$_b$; each R$_a$ independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl; and each R$_b$, independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{ao}$ cycloalkenyl, C$_1$-C$_{20}$ heterocycloalkyl, C$_1$-C$_{20}$ heterocycloalkenyl, aryl, or heteroaryl.

In some embodiments, n can be 0.

In some embodiments, m can be 1.

In some embodiments, R$_7$ can be halo (e.g., F, Cl, Br, or I).

In some embodiments, R$_7$ can be a substituent (e.g., halo such as F) at the para position.

In some embodiments, each of R$_1$, R$_2$, R$_3$, R$_4$, and R$_5$ can be H.

An example of the compounds of formula (I) is

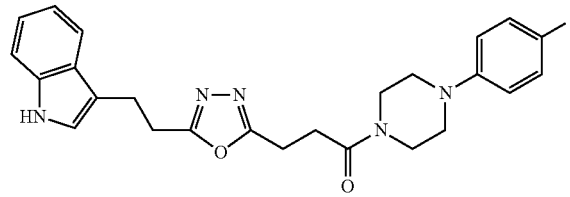

(i.e., Compound 1 and also referred to as DW0441).

The term "alkyl" refers to a saturated, linear or branched hydrocarbon moiety, such as —CH$_3$ or —CH(CH$_3$)$_2$. The term "alkenyl" refers to a linear or branched hydrocarbon moiety that contains at least one double bond, such as —CH═CH—CH$_3$. The term "alkynyl" refers to a linear or branched hydrocarbon moiety that contains at least one triple bond, such as —C≡C—CH$_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

In some embodiments, alkyl, haloalkyl, alkenyl, alkylene, heteroalkylene, alkynyl, cycloalkyl, heterocycloalkyl, aryl, phenylene, and heteroaryl mentioned herein can be further substituted. Possible substituents include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_3$-C$_{20}$ heterocycloalkyl, C$_3$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, C$_1$-C$_{20}$ dialkylamino, arylamino, diarylamino, hydroxyl, halogen, thio, C$_1$-C$_{10}$ alkylthio, arylthio, C$_1$-C$_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. Cycloalkyl, heterocycloalkyl, cycloalkenyl, heterocycloalkenyl, aryl, and heteroaryl can also be fused with each other.

In another aspect, this disclosure features compounds of formula (II) or a salt thereof (e.g., a pharmaceutically acceptable salt thereof):

(II)

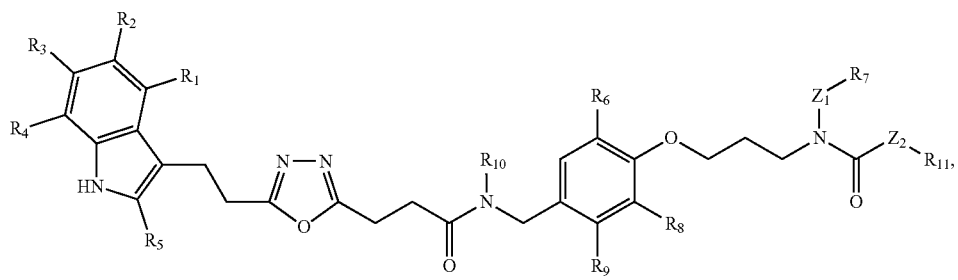

In formula (II), each of R$_1$, R$_2$, R$_3$, R$_4$, and R$_5$, independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, halo, OR$_a$, SR$_a$, COOR$_a$, OC(O)R$_a$, C(O)R$_a$, C(O)NR$_a$R$_b$, S(O)$_2$NR$_a$R$_b$, or NR$_a$R$_b$; each of R$_6$, R$_8$, R$_9$, independently, is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, halo, OR$_a$, SR$_a$, COOR$_a$, OC(O)R$_a$, C(O)R$_a$, C(O)NR$_a$R$_b$, S(O)$_2$NR$_a$R$_b$, or NR$_a$R$_b$; or R$_6$ and R$_7$, R$_8$, or R$_8$ and R$_9$, together with the carbon atoms to which they are attached, are aryl, heteroaryl, C$_3$-C$_{20}$ cycloalkyl, C$_1$-C$_{20}$ heterocycloalkyl, each R$_7$, and R$_{11}$, independently, is H, C$_1$-C$_{10}$ alkenyl, C$_1$-C$_{10}$ haloalkyl, C$_2$-C$_{10}$ alkenyl, or C$_2$-C$_{10}$ alkynyl, R$_{10}$ is C$_1$-C$_{10}$ alkyl; Z$_1$ is deleted or a divalent group consisting of any 1, 2, 3, 4, or 5 of the following independently selected moieties: (i) C$_{1-10}$ alkylene; (ii) heteroalkylene that spans from 3-20 atoms in length wherein from 1-8 of the atoms in the span are heteroatomic groups that are each independently selected from N, NH, N—C$_1$-C$_6$ alkyl, O, and S, provided that there is at least one carbon atom between the occurrence of any two heteroatomic groups; and (iii) —C(O)—, —OC (=O)—, —C(=O)O—, —NHC(=O)—, —C(=O)NH—, —NHC(=O)NH—, —NHC(=S)NH—, —OC(=O)NH—, and —NHC(=O)O—; $Z_2$ is a divalent group consisting of any 1, 2, 3, 4, or 5 of the following independently selected moieties: (i) $C_{1-10}$ alkylene; (ii) a diazidine ring; and (iii) a phenylene; each $R_a$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and each $R_b$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

In some embodiments, $Z_2$ in formula (II) is a divalent group consisting of any 1 or 2 of the following independently selected moieties: (i) $C_{1-4}$ alkylene; and (ii) a diazidine ring. In such embodiments, $Z_2$ can be

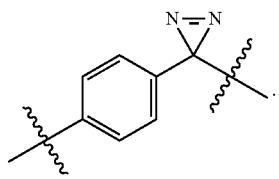 [SMILES: *c1ccc(C2(*)N=N2)cc1]

In some embodiments, $Z_2$ in formula (II) is a divalent group consisting of any 1 or 2 of the following independently selected moieties: a diazidine ring and a phenylene. In such embodiments, $Z_2$ can be

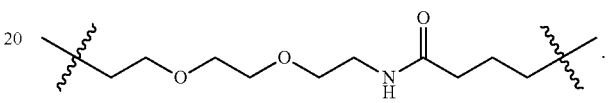

In some embodiments, $Z_1$ in formula (II) is deleted. In some embodiments, $Z_1$ in formula (II) is a divalent group consisting of any 1, 2, 3, 4, or 5 of the following independently selected moieties: (i) $C_{1-4}$ alkylene; (ii) heteroalkylene that spans from 3-10 atoms in length wherein from 1-3 of the atoms in the span are O, provided that there is at least one carbon atom between the occurrence of any two O atoms; and (iii) —NHC(=O)— and —C(=O)NH—. In such embodiments, $Z_1$ can be

[structure]

In some embodiments, $R_{11}$ in formula (II) is $C_2$-$C_{10}$ alkynyl or $C_1$-$C_4$ haloalkyl.

In some embodiments, each of $R_1$, $R_2$, $R_3$, $R_4$, $R_5$, $R_6$, $R_7$, $R_8$, $R_9$, and $R_{10}$ in formula (II), independently, is H or $C_1$-$C_{10}$ alkyl. In some embodiments, $R_7$ in formula (II) is $C_2$-$C_{10}$ alkynyl.

Examples of compounds of formula (II) include

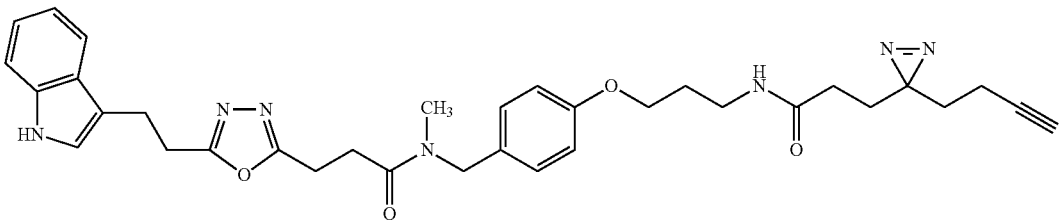 [SMILES: C#CCCC1(CCC(=O)NCCCOc2ccc(CN(C)C(=O)CCc3nnc(CCc4c[nH]c5ccccc45)o3)cc2)N=N1]

Compound 2 and also referred to as PAL-1) and

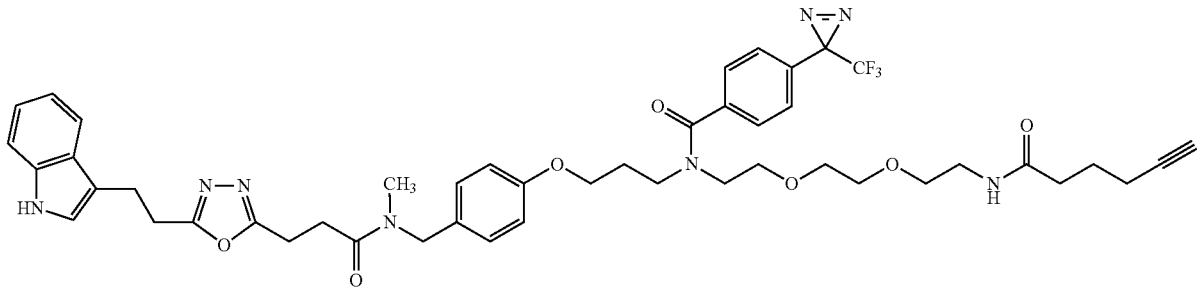 [SMILES: C#CCCCC(=O)NCCOCCOCCN(CCCOc1ccc(CN(C)C(=O)CCc2nnc(CCc3c[nH]c4ccccc34)o2)cc1)C(=O)c1ccc(C2(C(F)(F)F)N=N2)cc1]

(i.e., Compound 3 and also referred to as PAL-2).

In another aspect, this disclosure features compounds of formula (III) or a salt thereof (e.g., a pharmaceutically acceptable salt thereof):

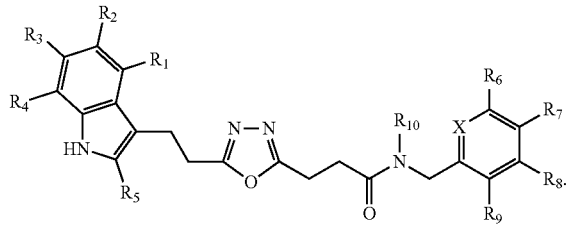

(III)

In formula (I), X is N or CH; each of $R_1$, $R_2$, $R_3$, $R_4$, and $R_5$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$; each of $R_6$, $R_7$, $R_8$, and $R_9$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$; or $R_6$ and $R_7$, $R_7$ and $R_8$, or $R_8$ and $R_9$, together with the carbon atoms to which they are attached, are aryl, heteroaryl, $C_3$-$C_{20}$ cycloalkyl, or $C_1$-$C_{20}$ heterocycloalkyl; $R_{10}$ is $C_1$-$C_{10}$ alkyl; each $R_a$ independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and each $R_b$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

Referring to formula (III), a subset of the compounds described above are those in which X is N. In such compounds, each of $R_1$, $R_2$, $R_3$, $R_4$, $R_5$, $R_6$, $R_7$, $R_8$, and $R_9$, independently, can be H or $C_1$-$C_{10}$ alkyl (e.g., $CH_2CH_3$). For example, in these compounds, $R_7$ can be $CH_2CH_3$ and $R_{10}$ can be $CH_3$. An example of such compounds is

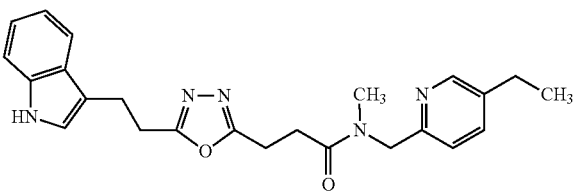 [SMILES: CCc1ccc(CN(C)C(=O)CCc2nnc(CCc3c[nH]c4ccccc34)o2)nc1]

(i.e., Compound 4 and also referred to as DW0069).

Referring to formula (III), another subset of the compounds described above are those in which X is CH. In such compounds, each of $R_1$, $R_2$, $R_3$, $R_4$, $R_5$, $R_6$, $R_7$, $R_8$, and $R_9$, independently, can be H or $C_1$-$C_{10}$ alkyl (e.g., $CH_2CH_3$). For example, in these compounds, $R_7$ can be $CH_2CH_3$ and $R_{10}$ can be $CH_3$. An example of such compounds is

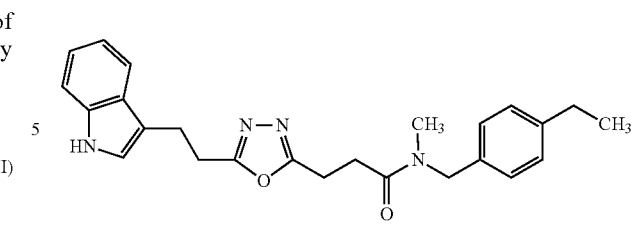

(i.e., Compound 5 and also referred to as DW0254).

In another aspect, this disclosure features a pharmaceutical composition that includes one or more of the compounds of formulas (I), (II), and (III) described above and a pharmaceutically acceptable carrier.

In another aspect, this disclosure features a method for treating a Rac-GTPase mediated disorder. The method includes administering to a subject in need thereof an effective amount of a compound of formula (I), (II), or (III), or the pharmaceutical composition described above containing a compound of formula (I), (II), or (III). Examples of Rac-GTPase mediated disorders include cardiovascular diseases, immunodeficiency diseases, inflammatory disorders and cancer. Examples of Rac include Rac1, Rac2, and Rac3. Examples of Rac-GTPase include Rac1-GTPase, Rac2-GTPase, and Rac3-GTPase.

The term "treating" or "treatment" refers to administering one or more of the compounds of formula (I), (II), and (III) described above to a subject who has an a disorder treatable with such compounds, and/or a symptom of such a disorder, and/or a predisposition toward such a disorder, with the purpose to confer a therapeutic effect, e.g., to cure, relieve, alter, affect, ameliorate, or prevent the above-described disorder, the symptom of it, or the predisposition toward it.

In another aspect, this disclosure features a method of harvesting hematopoietic cells from a subject. The method includes administering to the subject an effective amount of a compound of formula (I), (II), or (III) or the pharmaceutical composition described above containing a compound of formula (I), (II), or (III) (e.g., to mobilize the hematopoietic cells out of bone marrow), and collecting hematopoietic cells from the subject. In some embodiments, the pharmaceutical composition is administered parentally to the subject.

In another aspect, this disclosure features a method of killing cancerous stem cells (e.g., leukemia stem cells). The method includes administering to a subject in need thereof an effective amount of a compound of formula (I), (II), or (III) or the pharmaceutical composition described above containing a compound of formula (I), (II), or (III) to mobilize cancerous stem cells out of bone marrow, and administering to the subject an effective amount of an anti-cancer drug to kill the cancerous stem cells. In some embodiments, the cancerous stem cells (e.g., leukemia stem cells) could be treated or killed in situ by systemic administration to a subject in need thereof an effective amount of a compound of formula (I), (II), or (III) or the pharmaceutical composition described above containing a compound of formula (I). In some embodiments, the compound of formula (I), (II), or (III) or the pharmaceutical composition containing the compound of formula (I), (II), or (III) is administered parentally to the subject.

In another aspect, this disclosure features a method of treating a disorder associated with a protein that interacts with PDE6D in a subject. The method includes administering to the subject in need thereof an effective amount of a compound of formula (I), (II), or (III) or an effective amount of the pharmaceutical composition containing a compound of formula (I), (II), or (III). In some embodiments, the protein is a member of the Arf subfamily of the Ras superfamily. For example, the protein can be Arl2, Arl3, Rho6, H-Ras, Rheb, or $G\alpha_{il}$.

In another aspect, this disclosure features a method of treating a disorder (e.g., cancer) modulated by mTOR pathway in a subject. The method includes administering to the subject in need thereof an effective amount of a compound of formula (I), (II), or (III) or an effective amount of the pharmaceutical composition containing a compound of formula (I), (II), or In another aspect, this disclosure features a method of treating a PDE6D mediated disorder (e.g., cancer) in a subject. The method includes administering to the subject in need thereof an effective amount of a compound of formula (I), (II), or (III) or an effective amount of the pharmaceutical composition containing a compound of formula (I), (II), or (III).

In another aspect, this disclosure features a method of inhibiting Rac activity in a cell (e.g., in vitro, in vivo, or ex vivo). The method includes contacting the cell with an effective amount of a compound of formula (I), (II), or (III) or an effective amount of the pharmaceutical composition containing a compound of formula (I), (II), or (III).

In another aspect, this disclosure features a method of inhibiting Ras activity in a cell (e.g., in vitro, in vivo, or ex vivo). The method includes contacting the cell with an effective amount of a compound of formula (I), (II), or (III) or an effective amount of the pharmaceutical composition containing a compound of formula (I), (II), or (III).

In another aspect, this disclosure features a method of modulating trafficking of Ras in a cell (e.g., in vitro, in vivo, or ex vivo). The method includes contacting the cell with an effective amount of a compound of formula (I), (II), or (III) or an effective amount of the pharmaceutical composition containing a compound of formula (I), (II), or (III).

The compounds described herein include the compounds of formula (I), (II), or (III), as well as their salts, prodrugs, and solvates, if applicable. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the compounds of formula (I), (II), or (III) described above for use in treating an above-described disorder, and the use of such a composition for the manufacture of a medicament for the just-mentioned treatment.

The details of one or more embodiments are set forth in the description below. Other features, objects, and advantages will be apparent from the description, drawings, and claims.

DESCRIPTION OF DRAWINGS

Like reference symbols in the various drawings indicate like elements.

DETAILED DESCRIPTION

Figure 1C:
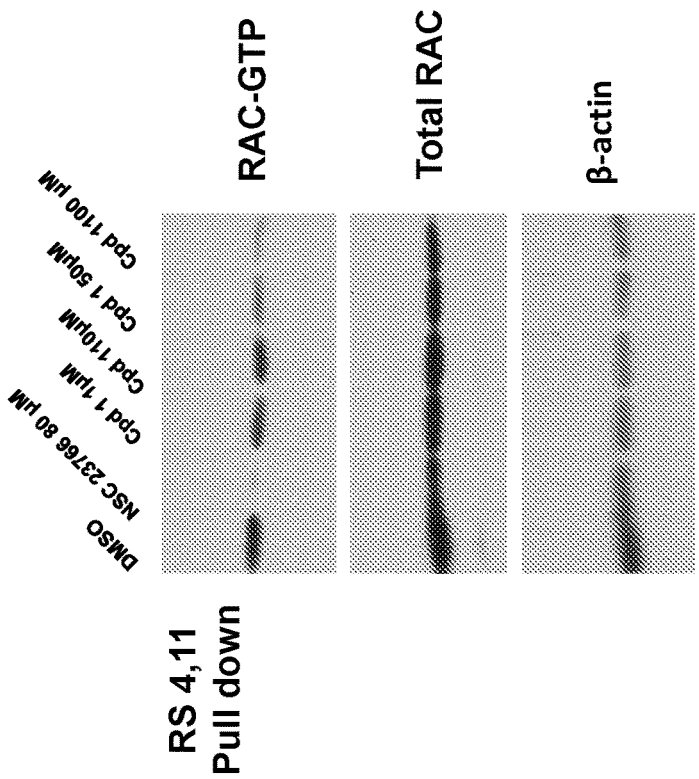
FIG. 1(c) shows a quantitation of pull down experiments obtained from DMSO, NSC23766, and Compound 1.

This disclosure relates to certain compounds of formulas (I), (II), and (III) identified as having anti-cancer activity using a quantitative, high throughput assay based on their inhibition of activation of the Rho family member Rac. The compounds unexpectedly exhibit inhibition of leukemia cell proliferation in vitro and, in the case of certain compounds, minimal toxicity to normal bone marrow cells. In some embodiments, the compounds of formulas (I), (II), and (III) can facilitate mobilization of hematopoietic stem cells out of bone marrow to harvest such cells or can facilitate mobilization of cancerous stem cells (e.g., leukemia stem cells) out of bone marrow to kill such cells.

All of the compounds described herein can be prepared by methods known in the art. A synthesized compound can be purified by a suitable method such as column chromatography, high-pressure liquid chromatography, or recrystallization.

The compounds described herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The compounds can be identified by a screening method, such as an assay that identifies compounds that inhibit the proliferation of cancer cells. Alternatively or in addition, compounds can be identified using an assay that identifies compounds that inhibit the activation of the target protein (e.g., Rac-GTPase) and/or by the in silico analysis of the compound docking on the structure of the target protein.

For example, the screening method can include exposing a leukemia cell line (e.g., REM, SEM, MV411, RS411, Jurkat, Raji, Nomo-1, Maim6, or ML2) to various doses of the compound for various time periods. A candidate compound that inhibits cell survival can be identified based on the ability of the cell to proliferate in the presence of the compound. Such a screening method can be carried out in a container that includes the cells from a specific cell line, liquid media, and a candidate compound. The container can be, for example, a petri dish, a tissue culture flask, 24-well plate, a 48-well plate, a 96-well plate, a 384-well plate, a 1536-well plate, a 3456-well plate, or any other suitable container. In a high throughput screening method, each well of the container may contain a different candidate compound. As would be appreciated in the art, the screening method may be automated to obtain high throughput. For example, an MTS assay can be performed in liquid medium in standard microtiter plates. In addition, because manual screening of the plates can be slow, labor intensive and subjective, an automated staining method can be used in a high throughput screening method to distinguish live from dead cells.

The present disclosure also provides pharmaceutical compositions that include at least one (e.g., at least 2, 3, 4, 5, or at least 6) compound(s) of formulas (I), (II), and (III) (e.g., Compounds 1-5), or a pharmaceutically acceptable salt thereof, and a pharmaceutically acceptable carrier.

Compounds described herein can induce inhibition of proliferation. Induction of the inhibition of proliferation can mean inducing or enhancing the suppression of proliferation signals in a cell. For example, induction of the inhibition of proliferation can mean inducing or enhancing cell death in a cell. As another example, induction of the inhibition of proliferation can mean inducing or enhancing apoptosis in a cell. As another example, induction of the inhibition of proliferation can mean inducing or enhancing the state of quiescence in a cell. As yet another example, induction of the inhibition of proliferation can mean inducing or enhancing autophagy. Accordingly, compounds described herein can be used in methods of inducing the suppression of proliferation in a cell. The methods can include contacting a cell with a compound, salt, or composition described herein, in an amount effective to induce suppression of proliferation in the cell. The contacting can be done in vivo, ex vivo, or in vitro.

Compounds described herein can inhibit activity of a protein, such as a Ras protein or a Rac protein, in a cell. In other words, the compounds described herein can be used as Ras or Rac inhibitors. In some embodiments, this disclosure features a method of inhibiting Ras or Rac activity in a cell. The method includes contacting the cell with a compound, salt, or composition described herein in an amount effective to inhibit the activity of a Ras or Rac protein. The contacting can be done in vivo, ex vivo, or in vitro. Without wishing to be bound by theory, it is believed that compounds described herein do not bind directly to Rac, but inhibit Rac activity by binding to PDE6D.

In some embodiments, this disclosure features a method of modulating trafficking of Ras in a cell (e.g., in vitro, in vivo, or ex vivo). The method includes contacting the cell with an effective amount of a compound of formula (I), (II), or (III) or an effective amount of the pharmaceutical composition containing a compound of formula (I), (II), or (III). For example, without wishing to be bound by theory, the compounds described herein can modulate trafficking of Ras (e.g., PDE6D/Arl2- or PDE6D/Arl3-dependent trafficking of Ras) by binding to PDE6D.

In some embodiments, this disclosure features a method for treating a Rac-GTPase mediated disorder. The method includes administering to a subject (e.g., a patient) in need thereof an effective amount of a compound of formula (I), (II), or (III) or an effective amount of the pharmaceutical composition containing a compound of formula (I), (II), or (III). Examples of Rac-GTPase mediated disorders include cardiovascular disease, immunodeficiency diseases, inflammatory disorders (e.g., autoimmune diseases), and cancer.

In some embodiments, this disclosure features a method for treating a PDE6D mediated disorder in a subject. The method includes administering to a subject (e.g., a patient) in need thereof an effective amount of a compound of formula (I), (II), or (III) or an effective amount of the pharmaceutical composition containing a compound of formula (I), (II), or (III). Examples of PDE6D mediated disorders include Joubert Syndrome, Orofaciodigital Syndrome, and cancers (e.g., leukemia, glioma, thyroid cancer, lung cancer such as non-small cell lung cancer, gastric cancer, liver cancer, pancreatic cancer, head and neck cancer, stomach cancer, colorectal cancer, urothelial cancer, renal cancer, prostate cancer, testis cancer, breast cancer, cervical cancer, ovarian cancer, endometrial cancer, melanoma, non-Hodgkin lymphoma, osteosarcoma, or hepatocellular carcinoma). In some embodiments, PDE6D mediated disorders can be Ras mediated disorders (e.g., Ras mediated cancers).

In some embodiments, this disclosure features a method for treating a disorder associated with a protein that interacts with PDE6D in a subject. The method includes administering to a subject (e.g., a patient) in need thereof an effective amount of a compound of formula (I), (II), or (III) or an effective amount of the pharmaceutical composition containing a compound of formula (I), (II), or (III). In some embodiments, the protein that interacts with PDE6D is a member of the Arf subfamily of the Ras superfamily. For example, the protein can be Arl2, Arl3, Rho6, H-Ras, Rheb, or Gad. In some embodiments, a disorder associated with a protein is a PDE6D mediated disorder described above.

In some embodiments, this disclosure features a method for treating a disorder modulated by or associated with mammalian target of rapamycin (mTOR) pathway (e.g., modulated by or associated with mTORC1 signaling) in a subject. The method includes administering to a subject (e.g., a patient) in need thereof an effective amount of a compound of formula (I), (II), or (III) or an effective amount of the pharmaceutical composition containing a compound of formula (I), (II), or (III). Examples of disorders modulated by or associated with mTOR pathway include cancers (e.g., leukemia, glioma, thyroid cancer, lung cancer such as non-small cell lung cancer, gastric cancer, liver cancer, pancreatic cancer, head and neck cancer, stomach cancer, colorectal cancer, urothelial cancer, renal cancer, prostate cancer, testis cancer, breast cancer, cervical cancer, ovarian cancer, endometrial cancer, melanoma, non-Hodgkin lymphoma, osteosarcoma, or hepatocellular carcinoma).

In some embodiments, this disclosure features a method for treating a SEPT11 mediated disorder in a subject. The method includes administering to a subject (e.g., a patient) in need thereof an effective amount of a compound of formula (I), (II), or (III) or an effective amount of the pharmaceutical composition containing a compound of formula (I), (II), or (III). Examples of SEPT11 mediated disorders include cancers (e.g., leukemia, glioma, thyroid cancer, lung cancer such as non-small cell lung cancer, gastric cancer, liver cancer, pancreatic cancer, head and neck cancer, stomach cancer, colorectal cancer, urothelial cancer, renal cancer, prostate cancer, testis cancer, breast cancer, cervical cancer, ovarian cancer, endometrial cancer, melanoma, non-Hodgkin lymphoma, osteosarcoma, or hepatocellular carcinoma).

The term "subject" is used throughout the disclosure to describe an animal, human or non-human, to whom treatment according to the methods described herein is provided. The term includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

Examples of cellular proliferative and/or differentiative disorders include cancer, such as carcinoma, sarcoma, metastatic disorders, and hematopoietic neoplastic disorders (e.g., leukemias and lymphomas).

A metastatic tumor can arise from a multitude of primary tumor types, including but not limited to, those of prostate, colon, lung, breast, bone, and liver origin. Metastases develop, e.g., when tumor cells shed from a primary tumor adhere to vascular endothelium, penetrate into surrounding tissues, and grow to form independent tumors at sites separate from a primary tumor.

The term "cancer" refers to cells having the capacity for autonomous growth. Examples of such cells include cells having an abnormal state or condition characterized by rapidly proliferating cell growth. The term is meant to include cancerous growths, e.g., tumors (e.g., solid tumors), oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems, as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

Cancers that may be treated using the methods and compositions of the present disclosure include, for example, cancers of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and throat; Hodgkins disease, leukemia, sarcomas, choriocarcinoma, and lymphoma, among others. Examples of leukemia include lymphocytic leukemia (e.g., acute lymphoblastic leukemia, pediatric acute lymphocytic leukemia, or B-cell chronic lymphocytic leukemia), chronic myelogenous leukemia, and non-Hodgkins leukemia.

Individuals considered at risk for developing cancer may benefit particularly from the invention, primarily because prophylactic treatment can begin before there is any evidence of the disorder. Individuals "at risk" include, e.g., individuals exposed to carcinogens (e.g., by consumption such as by inhalation and/or ingestion) at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals in very early stages of cancer or development of metastases (i.e., only one or a few aberrant cells are present in the individual's body or at a particular site in an individual's tissue)) may benefit from such prophylactic treatment.

Other examples of cellular proliferative and/or differentiative disorders that can be treated by the compounds described herein include inflammatory diseases and bone resorption disorders. Examples of inflammatory disorders include autoimmune disease, neurodegenerative disease, multiple sclerosis, systemic lupus erythematosus, rheumatoid arthritis, atherosclerosis, encephalitis, meningitis, hepatitis, nephritis, sepsis, sarcoidosis, psoriasis, eczema, uticaria, Type I diabetes, asthma, conjunctivitis, otitis, allergic rhinitis, chronic obstructive pulmonary disease, sinusitis, dermatitis, inflammatory bowel disease, ulcerative colitis, Crohn's disease, Behcet's syndrome, gout, viral infections, bacterial infections, organ transplant conditions, skin transplant conditions, graft rejection (including allograft rejection and graft-versus-host disease), spondyloarthropathies, scleroderma, vasculitis, and psoriasis (including T-cell mediated psoriasis). Other inflammatory disorders have been described in, e.g., U.S. Application Publication No. 20020155166, the entire contents of which are herein incorporated by reference.

In some embodiments, this disclosure features a method of treating unwanted angiogenesis in a patient. The method includes administering to a patient diagnosed as suffering from or at risk for unwanted angiogenesis an effective amount of a pharmaceutical composition containing one or more of the compounds described herein. The method can optionally include a step of identifying (e.g., diagnosing) the patient as suffering from or at risk for unwanted angiogenesis.

In some embodiments, this disclosure features a method of treating a condition associated with unwanted angiogenesis. The method includes administering to a patient diagnosed as suffering from or at risk for a condition associated with unwanted angiogenesis an effective amount of a pharmaceutical composition containing one or more of the compounds described herein, wherein the condition associated with unwanted angiogenesis is not cancer. The method can optionally include a step of identifying (e.g., diagnosing) the patient as suffering from or at risk for a condition associated with unwanted angiogenesis. In an embodiment, the condition is rheumatoid arthritis, lupus, psoriasis, diabetic retinopathy, retinopathy of prematurity, macular degeneration, corneal graft rejection, neovascular glaucoma, retrolental fibroplasia, rubeosis, Osler-Weber Syndrome, myocardial angiogenesis, plaque neovascularization, telangiectasia, or angiofibroma, or any combination thereof.

Methods of Treatment

Skilled practitioners will appreciate that a patient can be diagnosed by a physician (or veterinarian, as appropriate for the patient being diagnosed) as suffering from or at risk for a condition described herein (e.g., cancer) by any method known in the art, such as by assessing a patient's medical history, performing diagnostic tests, and/or by employing imaging techniques.

Skilled practitioners will also appreciate that compositions described herein need not be administered to a patient by the same individual who diagnosed the patient (or prescribed the composition for the patient). The compositions can be administered (and/or administration can be supervised), e.g., by the diagnosing and/or prescribing individual, and/or any other individual, including the patient her/himself (e.g., where the patient is capable of self-administration).

Amounts of the composition effective to treat a disorder described herein (e.g., cancer) can be administered to (or prescribed for) a patient, e.g., by a physician or veterinarian, on the day the patient is diagnosed as suffering any of these disorders or conditions, or as having any risk factor associated with an increased likelihood that the patient will develop such disorder(s) or condition(s) (e.g., the patient has recently been, is being, or will be exposed to a carcinogen (s)). The composition can be administered to the patient intermittently or continuously. For example, the composition can be administered for at least about 1, 2, 4, 6, 8, 10, 12, 14, 18, or 20 days, or greater than 20 days (e.g., 1 2, 3, 5, or 6 months) or until the patient no longer exhibits symptoms of the condition or disorder, or until the patient is diagnosed as no longer being at risk for the condition or disorder. In a given day, a composition can be administered continuously for the entire day, or intermittently or for up to 23 hours per day, e.g., up to 20, 15, 12, 10, 6, 3, or 2 hours per day, or up to 1 hour per day.

If the patient needs to be treated with chemotherapy, radiation therapy, immunotherapy, gene therapy, and/or surgery (e.g., because prescribed by a physician or veterinarian), the patient can be treated with a composition described herein before, during, and/or after administration of the chemotherapy, radiation therapy, and/or surgery. For example, with regard to chemotherapy, immunotherapy, gene therapy, and radiation therapy, a composition can be administered to the patient, intermittently or continuously, starting 0 to 20 days before the chemotherapy, immunotherapy, gene therapy, or radiation therapy is administered (and where multiple doses are given, before each individual dose), e.g., starting at least about 30 minutes (e.g., about 1, 2, 3, 5, 7, or 10 hours, or about 1, 2, 4, 6, 8, 10, 12, 14, 18, or 20 days, or greater than 20 days) before the administration. Alternatively or in addition, the composition can be administered to the patient concurrently with administration of chemotherapy, immunotherapy, gene therapy, or radiation therapy. Alternatively or in addition, the composition can be administered to the patient after administration of chemotherapy, immunotherapy, gene therapy, or radiation therapy, e.g., starting immediately after administration, and continuing intermittently or continuously for about 1, 2, 3, 5, 7, or 10 hours, or about 1, 2, 5, 8, 10, 20, 30, 50, or 60 days, one year, indefinitely, or until a physician determines that administration of the composition is no longer necessary. With regard to surgical procedures, the composition can be administered systemically or locally to a patient prior to, during, and/or after a surgical procedure is performed. The composition can be administered to the patient intermittently or continuously, for 1 hour, 2, hours, 3 hours, 4 hours, 6, hours, 12 hours, or about 1, 2, 4, 6, 8, 10, 12, 14, 18, or 20 days, or greater than 20 days, before the procedure. It can be administered in the time period immediately prior to the surgery and optionally continue through the procedure, or the administration can cease at least 15 minutes (e.g., at least 30 minutes, 1 hour, 2 hours 3 hours, 6 hours, or 24 hours) before the surgery begins. Alternatively or in addition, the composition can be administered to the patient during the procedure, e.g., by topical administration. Alternatively or in addition, the composition can be administered to the patient after the procedure, e.g., starting immediately after completion of the procedure, and continuing for about 1, 2, 3, 5, 7, or 10 hours, or about 1, 2, 5, 8, 10, 20, 30, 50, or 60 days, 1 year, indefinitely, or until the patient no longer suffers from, or is at risk for, cancer after the completion of the procedure.

Treatments for B-cell chronic lymphocytic leukemia (B-CLL) can include administration of combination chemotherapeutic regimens. In many instances, combinations of fludarabine with alkylating agents or with monoclonal antibodies can be used for the treatment of B-CLL. For example, fludarabine can be administered in a combination therapy with alkylating agents such as cyclophosphamide or bendamustine. Fludarabine can also be administered in combination with monoclonal antibodies such as alemtuzumab, rituximab, or ofatumumab. Fludarabine can also be administered for the treatment of B-CLL in combination with all of the following: an alkylating agent, an anthracycline antibiotic, a vinca alkyloid, and a corticosteroid. For example, fludarabine can be administered together with cyclophosphamide, doxorubicin, vincristine and prednisolone.

Treatments for acute lymphoblastic leukemia (ALL) can include administration of the following: prednisone, vincristine, anthracyclines, L-asparaginase, cyclophosphamide.

Treatments for chronic myelogenous leukemia (CML) can include the administration of imatinib. Treatments for prolymphocytic leukemia can include purine analogues, chlorambucil, and various chemotherapy including: cyclophosphamide, doxorubicin, vincristine, prednisone cyclophosphamide, doxorubicin, vincristine and prednisolone, etoposide, bleomycin VAPEC-B, and Alemtuzumab.

Treatments for the diseases encompassing leukemia can include the following therapeutic agents and combinations of these therapeutic regimens: In many instances, combinations of fludarabine, alkylating agents such as cyclophosphamide or bendamustine, monoclonal antibodies such as alemtuzumab, rituximab, or ofatumumab, an anthracycline antibiotic such as doxirubicin, a vinca alkyloid, anthracyclines, L-asparaginase, cyclophosphamide, imatinib, purine analogues, chlorambucil, cyclophosphamide, doxorubicin, vincristine, prednisone cyclophosphamide, doxorubicin, vincristine and prednisolone, etoposide, bleomycin VAPEC-B, and Alemtuzumab and/or a corticosteroid.

Combination Therapy

In some embodiments, a compound of formula (I), (II), or (III) described in the present disclosure, or a pharmaceutically acceptable salt thereof, can be used in combination with another therapeutic agent to treat diseases such as cancer. For example, the additional agent can be a therapeutic agent that is art-recognized as being useful to treat the disease or condition being treated by the compound described above. In some embodiments, the additional agent can be an anti-cancer drug, such as Dexamethasone, Vincristine, or a PAK inhibitor (e.g., PF-3758309 described in Murray et al., *PNAS*, Vol. 107, No. 20, 9446-9451 (2010)). The additional agent also can be an agent that imparts a beneficial attribute to the therapeutic composition (e.g., an agent that affects the viscosity of the composition).

The combination therapy contemplated by this disclosure includes, for example, administration of one or more compound described herein, or a pharmaceutically acceptable salt thereof, and additional agent(s) in a single pharmaceutical formulation or in separate pharmaceutical formulations. Alternatively or in addition, combination therapy can include administering at least two compounds described herein, or pharmaceutically acceptable salts thereof, in the same or separate pharmaceutical formulations. In other words, co-administration shall mean the administration of at least two agents to a subject so as to provide the beneficial effects of the combination of both agents. For example, the agents may be administered simultaneously or sequentially over a period of time.

In some embodiments, the methods described herein can be used in combination with the therapies and combination therapies recited above. For example, a compound of formula (I), (II), or (III) described herein can be administered (e.g., parentally) to a subject at a specific target site to mobilize cancerous stem cells (e.g., leukemia stem cells) out of bone marrow. The subject can then be administered (e.g., orally) with an anti-cancer drug (such as those described above) to kill the cancerous stem cells.

Methods of Harvesting Hematopoietic Cells

In some embodiments, a compound of formula (I), (II), or (III) described in the present disclosure, or a pharmaceutically acceptable salt thereof, can be used to harvest hematopoietic cells (e.g., hematopoietic stem cells). Thus, the present disclosure also features a method that includes administering to the subject an effective amount of a compound of formula (I), (II), or (III) or the pharmaceutical composition described herein containing a compound of formula (I), (II), or (III) (e.g., to mobilize the hematopoietic cells out of bone marrow). In some embodiments, the method further includes collecting hematopoietic cells from the subject. The compound of formula (I), (II), or (III) can be administered to the subject in any means or at any frequency that are deemed appropriate by a physician (such as those described in the present disclosure). For example, the compound of formula (I), (II), or (III) can be administered to the subject parentally. Without wishing to be bound by theory, it is believed that the compounds of formulas (I), (II), or (III) can facilitate mobilizing hematopoietic cells from the bone marrow and thereby facilitating harvesting these hematopoietic cells.

Pharmaceutical Formulations and Dosage Forms

When employed as pharmaceuticals, the compounds described in the present application can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also within the scope of this disclosure are pharmaceutical compositions containing at least one compound described above and a pharmaceutical acceptable carrier. Further, this disclosure covers a method of administering an effective amount of the compounds described herein, e.g., in a pharmaceutical composition, to a patient having cancer, such as described herein. "An effective amount" or "an amount effective" refers to the amount of an active compound that is required to confer a therapeutic effect on the treated patient. Effective doses will vary, as recognized by those skilled in the art, depending on the types of diseases treated, route of administration, excipient usage, and the possibility of co-usage with other therapeutic treatment.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the treatment method described herein, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typical doses can range from about 0.01 µg/kg to about 50 mg/kg (e.g., from about 0.1 µg/kg to about 25 mg/kg, from about 1 µg/kg to about 10 mg/kg, from about 10 µg/kg to about 5 mg/kg, or from about 0.1 mg/kg to about 1 mg/kg) of body weight per day. In some embodiments, suitable daily doses can range from about 10 µg/kg to about 100 µg/kg of body weight.

To practice the method described in the present disclosure, a composition having one or more compounds described above can be administered parenterally, orally, nasally, rectally, topically, and/or buccally. The term "parenteral" as used herein refers to subcutaneous, intracutaneous, intravenous, intramuscular, intraarticular, intraarterial, intrasynovial, intrasternal, intrathecal, intralesional, intraperitoneal, or intracranial injection, as well as any suitable infusion technique.

A sterile injectable composition can be a solution or suspension in a non-toxic parenterally acceptable diluent or solvent, such as a solution in buffered saline or 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as TWEENs or SPANs or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds described above can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The therapeutic compounds can also be prepared with carriers that protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of formulating suitable pharmaceutical compositions are known in the art. See, e.g., the books in the series *Drugs and the Pharmaceutical Sciences: a Series of Textbooks and Monographs* (Dekker, N.Y.).

The compounds described above can be preliminarily screened for their efficacy in treating above-described diseases by the screening method described herein and then confirmed by additional animal experiments and/or clinic trials. Other screening methods will also be apparent to those of ordinary skill in the art.

Synthesis

Compounds described in this disclosure, including salts thereof, can be prepared using known organic synthesis techniques and can be synthesized according to any of numerous possible synthetic routes, for example, by methods analogous to those of Gerard et al. *ACS Comb. Sci.* 2011, 13, 365. Example 1 below provide detailed descriptions of the preparation of Compound 1. Other compounds of formula (I) or compounds of formulas (II) and (III) can be synthesized in a similar manner.

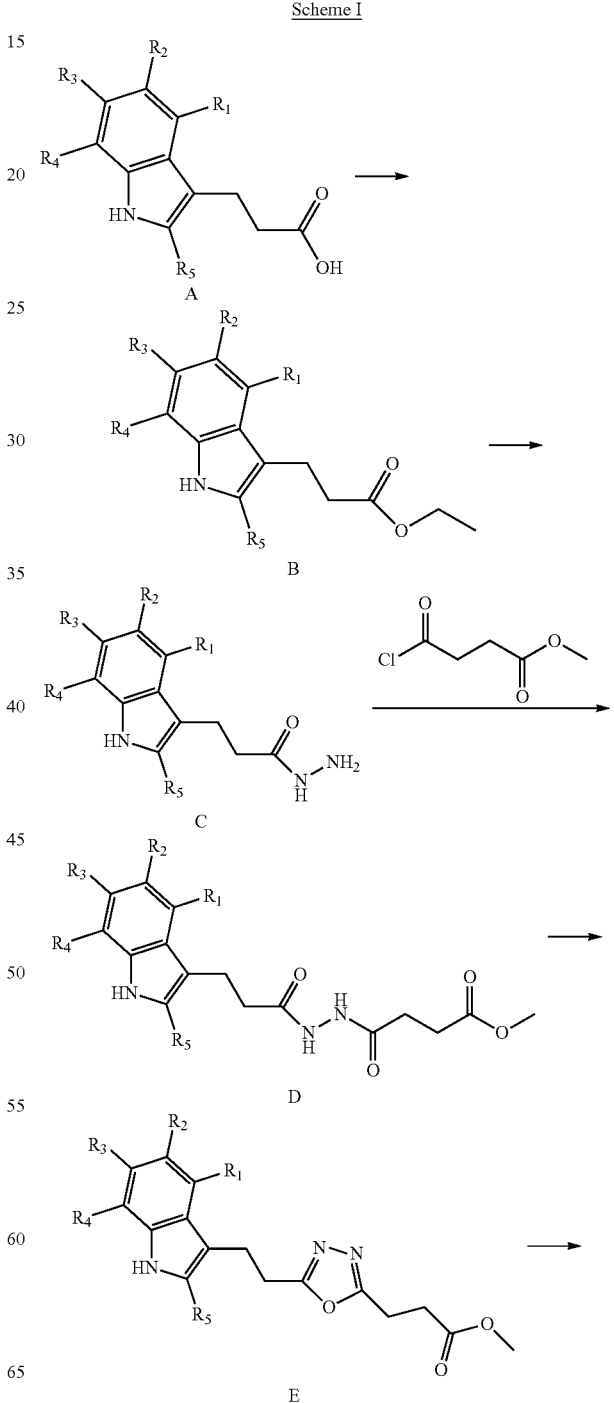

Scheme I

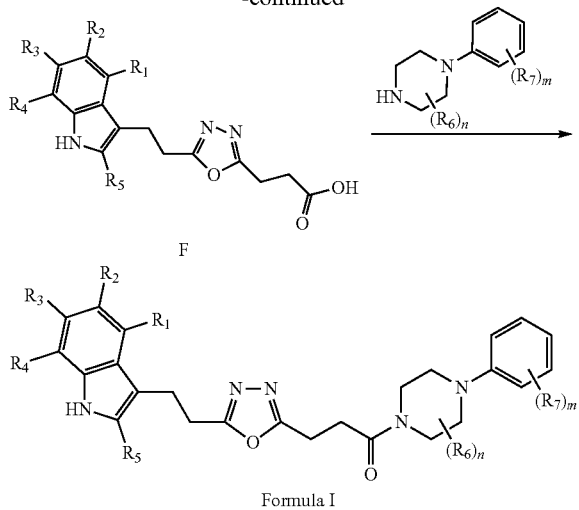

Formula I

Scheme I shown above depicts a typical synthetic route for synthesizing the compounds of formula (I). Specifically, an indole compound containing a carboxylate group (i.e., compound A) can first be converted to an ester compound (i.e., compound B). The ester compound can then react with a hydrazine to afford a corresponding hydrazide (i.e., compound C), which can react with methyl 4-chloro-4-oxobutanoate to form a substituted hydrazide compound (i.e., compound D) containing two carbonyl groups neighboring the hydrazide group. These two carbonyl groups on the substituted hydrazide compound can react with a Bergess reagent to form a compound containing a (i.e., compound E). The compound thus formed can first be converted to an acid (i.e., compound F), which can then react with a substituted piperazine compound to form a compound of formula (I) (e.g., Compound 1).

The reactions for preparing compounds of the present application can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described in the present application can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC).

Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the present application also include tautomeric forms. Tautomeric forms result from the swapping of a single bond with an adjacent double bond together with the concomitant migration of a proton. Tautomeric forms include prototropic tautomers, which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described in the present application can also include all isotopes of atoms occurring in the intermediates or final compounds. Isotopes include those atoms having the same atomic number but different mass numbers. For example, isotopes of hydrogen include tritium and deuterium.

All compounds and pharmaceutically acceptable salts thereof, can be found together with other substances such as water and solvents (e.g. hydrates and solvates) or can be isolated.

In some embodiments, the compounds described in the present application, or salts thereof, are substantially isolated. By "substantially isolated" is meant that the compound is at least partially or substantially separated from the environment in which it was formed or detected. Partial separation can include, for example, a composition enriched in the compounds described in the present application. Substantial separation can include compositions containing at least about 50%, at least about 60%, at least about 70%, at least about 80%, at least about 90%, at least about 95%, at least about 97%, or at least about 99% by weight of the compounds described in the present application, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Kits

The present disclosure also includes pharmaceutical kits useful, for example, in the treatment or prevention of a Rac-GTPase mediated disorder (e.g. cancer), which include one or more containers containing a pharmaceutical composition comprising a therapeutically effective amount of a compound of the present application. Such kits can further include, if desired, one or more of various conventional pharmaceutical kit components, such as, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The contents of all publications cited herein (e.g., patents, patent application publications, and articles) are hereby incorporated by reference in their entirety.

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1: Synthesis of Compound 1

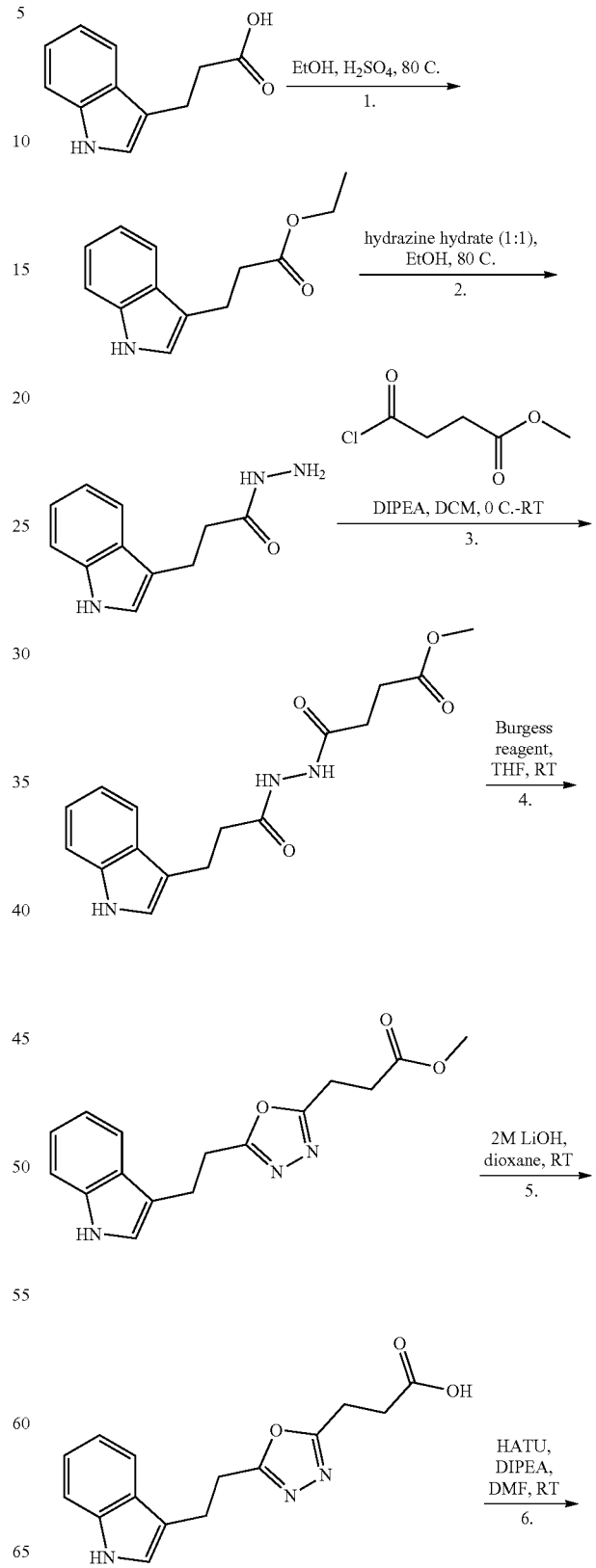

-continued

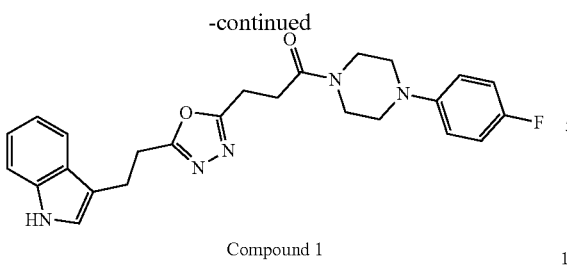

Compound 1

Step 1—Synthesis of ethyl 3-(1H-indol-3-yl)propanoate

In an round bottom flask, 3-(1H-indol-3-yl)propanoic acid (8 g, 0.04 mol) was dissolved in EtOH (80 mL). The mixture was cooled to 0° C. and then sulphuric acid (1.6 mL) was added drop-wise over five minutes with stirring. After the addition was complete, the mixture was allowed to warm naturally to room temperature with stirring and was then refluxed at 80° C. until completion (overnight). After the solvent was removed under reduced pressure, dichloromethane (10 mL) was added and the organic layer was washed with water (1×10 mL), followed by $NaHCO_3$ (1×10 mL) and finally brine (1×10 mL). The organic layers were then dried ($MgSO_4$) and concentrated to yield a crude brown oil which solidified on standing. The crude material was triturated with heptane (10 mL) and the solid was filtered under vacuum to yield the desired product as an off white solid (7.1 g, 74%). LC/MS (METCR1673 Generic 2 minutes) $t_r$=1.28 min, 96%, m/z=217.95 [M+H]. 1H NMR (250 MHz, Chloroform-d) δ7.98 (s, 1H), 7.69-7.52 (m, 1H), 7.43-7.30 (m, 1H), 7.29-7.07 (m, 2H), 7.05-6.92 (m, 1H), 4.15 (q, J=7.1 Hz, 2H), 3.25-3.01 (m, 2H), 2.72 (dd, J=8.4, 6.9 Hz, 2H), 1.25 (t, J=7.1 Hz, 3H).

Step 2—Synthesis of 3-(1H-indol-3-yl)Propanehydrazide

This reaction was carried out in a round bottom flask with a condenser. Specifically, hydrazine hydrate (1:1) (15.21 ml, 311.95 mmol) was added drop-wise to a stirred solution of ethyl 3-(1H-indol-3-yl)propanoate (96%, 7.06 g, 31.2 mmol) dissolved in ethanol (35 mL) at room temperature. The reaction was heated to 80° C. and stirred overnight. Upon completion the reaction was allowed to cool naturally to room temperature with stirring. Water (10 mL) was then added and the reaction mixture was concentrated under reduced pressure to yield an off white solid in a slurry of approximately 5 mL of water. After the slurry was filtered under vacuum, the solid was further washed with water (3×10 mL) to yield the desired product as an off white solid (5.8 g, 90%). LC/MS (METCR1673 Generic 2 minutes) $t_r$=0.76 min, 98%, m/z=204.00 [M+H]. 1H NMR (250 MHz, DMSO-d6) δ10.76 (s, 1H), 9.01 (s, 1H), 7.51 (d, J=7.8 Hz, 1H), 7.37-7.23 (m, 1H), 7.14-6.91 (m, 3H), 3.00-2.84 (m, 2H), 2.39 (dd, J=8.6, 6.9 Hz, 2H).

Step 3—Synthesis of methyl 4-[3-(1H-indol-3-yl) propanehydrazido]-4-oxobutanoate 3-(1H-indol-3-yl)propanehydrazide (96%, 2.02 g, 9.56 mmol) was suspended in dichloromethane (25 ml). N,N-Diisopropylethylamine (2.08 ml, 11.96 mmol) was added and the reaction was stirred at 0° C. under $N_2$ for ten minutes. A solution of methyl 4-chloro-4-oxobutanoate (0.98 ml, 7.97 mmol) in dichloromethane (5 mL) was then added drop-wise over twenty minutes. Once addition was complete, the reaction was allowed to warm naturally to room temperature and stirred for one hour. A further 0.2 eq of methyl 4-chloro-4-oxobutanoate in dichloromethane (1 mL) was then added to the reaction mixture drop-wise at 0° C. with stirring and the reaction stirred for a further hour at room temperature. After one hour, the off white suspension was filtered under vacuum. The solid was further washed with dichloromethane (5 ml) to yield the desired product as a white solid (1.98 g, 70%). LC/MS (METCR1673 Generic 2 minutes) $t_r$=0.87 min, 90%, m/z=317.95 [M+H]. 1H NMR (250 MHz, DMSO-d6) δ10.78 (s, 1H), 9.81 (s, 2H), 7.52 (d, J=7.7 Hz, 1H), 7.32 (d, J=7.9 Hz, 1H), 7.20-6.88 (m, 3H), 3.58 (s, 3H), 2.93 (t, J=7.7 Hz, 2H), 2.72-2.30 (m, part obsc, 4H), 1.25 (d, J=5.6 Hz, 2H).

Step 4—Synthesis of Methyl 3-{5-[2-(1H-indol-3-yl)ethyl]-1,3,4-oxadiazol-2-yl}Propanoate To a stirred solution of methyl 4 [3-(1H-indol-3-yl)propanehydrazido]-4-oxobutanoate obtained in step 3 (90%, 1.95 g, 5.53 mmol) in dry THF (15 ml) was added 3,3,3-triethyl-1-(methoxycarbonyl)diazathian-3-ium-1-ide 2,2-dioxide (Burgess reagent) (2.65 g, 11.06 mmol). The reaction was stirred at room temperature for two hours. After addition of Burgess reagent, the reaction mixture turned from a cloudy suspension to a clear solution. After two hours, a precipitate had crashed out. The reaction was filtered under vacuum to remove the solid, which was found not to be the desired product. The solid was washed further with THF (10 mL). The filtrate was concentrated under reduced pressure to yield a pale straw solid which was then triturated with DCM/heptane. A white solid crashed out and was filtered under vacuum to yield the desired product as a white solid (1.66 g, 53%). LC/MS (METCR1673 Generic 2 minutes) $t_r$=1.01 min, 97%, m/z=299.95 [M+H]. 1H NMR (500 MHz, DMSO-d6) δ10.81 (s, 1H), 7.49 (d, J=7.8 Hz, 1H), 7.33 (d, J=8.1 Hz, 1H), 7.13 (d, J=2.3 Hz, 1H), 7.10-7.04 (m, 1H), 7.01-6.95 (m, 1H), 3.61 (s, 3H), 3.20-3.14 (m, 2H), 3.14-3.08 (m, 2H), 3.04 (t, J=7.1 Hz, 2H), 2.77 (t, J=7.1 Hz, 2H).

Step 5—Synthesis of 3-{5-[2-(1H-indol-3-yl)ethyl]-1,3,4-oxadiazol-2-yl}propanoic Acid Methyl 3-{5 [2-(1H-indol-3-yl)ethyl]-1,3,4-oxadiazol-2-yl}propanoate obtained from step 4 (97%, 650 mg, 2.01 mmol) was suspended in dioxane (10 mL). 2M LiOH (2.01 mL) was added and the reaction was stirred at room temperature until completion. Upon completion, the reaction mixture was concentrated under reduced pressure to yield a white powder. Water (5 mL) was added and then the mixture was extracted with dichloromethane (2×5 mL). The organic layers were separated by passing through a hydrophobic frit. The basic aqueous was then acidified to pH=1 (2M HCl), resulting in a white solid crashing out. The white solid was filtered under vacuum, and washed further with water (10 mL) to yield the desired product as a white solid (0.6 g, 99%). LC/MS (METCR1673 Generic 2 minutes) $t_r$=0.92 min, 99%, m/z=285.90 [M+H]. 1H NMR (250 MHz, DMSO-d6) δ12.36 (s, 1H), 10.80 (s, 1H), 7.49 (d, J=7.8 Hz, 1H), 7.39-7.26 (m, 1H), 7.14 (d, J=2.4 Hz, 1H), 7.07 (td, J=8.2, 7.6, 1.3 Hz, 1H), 6.97 (td, J=7.5, 7.0, 1.1 Hz, 1H), 3.22-3.06 (m, 4H), 3.00 (t, J=7.1 Hz, 2H), 2.69 (t, J=7.1 Hz, 2H).

Step 6—Synthesis of 1-[4-(4-fluorophenyl)piperazin-1-yl]-3-{5-[2-(1H-indol-3-yl)ethyl]-1,3,4-oxadiazol-2-yl}propan-1-one (General HATU Coupling Procedure)

3-{5-[2-(1H-indol-3-yl)ethyl]-1,3,4-oxadiazol-2-yl}propanoic acid obtained from step 5 (99%, 50 mg, 0.18 mmol), 1-(4-fluorophenyl)piperazine (31.58 mg, 0.18 mmol) and N,N-diisopropylethylamine (115.86 µl, 0.7 mmol) were dissolved in DMF (dry) (1.5 mL). HATU (99.96 mg, 0.26 mmol) was added and the reaction was stirred at room temperature until completion. After the reaction mixture was concentrated under reduced pressure, dichloromethane (5 mL) and $H_2O$ (5 mL) were added. The organic layer was separated via a PTFE fritted tube and concentrated under reduced pressure. The residue was purified by basic prep (Gilson 5) and acidic prep (Gilson 7) to obtain 47.7 mg (60.2%) of 1-[4-(4-fluorophenyl)piperazin-1-yl]-3-{5-[2-(1H-indo-3-yl)ethyl]-1,3,4-oxadiazol-2-yl}propan-1-one (Compound 1) as an off-white solid. LC/MS (MET-uPLC-AB-101 (MSQ1, 7 min, low pH)) $t_r$=3.16 min, 99%, m/z=448 [M+H]. 1H NMR (500 MHz, Chloroform-d) δ8.03 (s, 1H), 7.57 (d, J=7.9 Hz, 1H), 7.36 (d, J=8.1 Hz, 1H), 7.23-7.18 (m, 1H), 7.16-7.10 (m, 1H), 7.06-7.03 (m, 1H), 7.01-6.95 (m, 2H), 6.91-6.86 (m, 2H), 3.84-3.72 (m, 2H), 3.70-3.60 (m, 2H), 3.31-3.24 (m, 2H), 3.24-3.19 (m, 2H), 3.16 (dd, J=8.3, 6.6 Hz, 2H), 3.12-3.08 (m, 2H), 3.08-3.04 (m, 2H), 2.88 (dd, J=8.2, 6.7 Hz, 2H).

Example 2: Analysis of Compound 1 of its Efficacy in Inhibiting Leukemia Cell Lines A formulation containing Compound 1 at 10 mg/mL in NMP/Eudragit L100-55/PEG200/Water at a ratio of 15/2/60/25 v/w/v/v was prepared as following: 10 mg of Compound 1 was mixed with 150.0 µL of NMP. Vortex and sonicating were used if necessary to avoid particle in suspension. A clear solution was obtained without any particles in suspension. To the above solution was added 20 mg of Eudragit L100-55 under stirring. The mixture was sonicated for 5 minutes and stirred with a magnetic bar for up to 60 minutes until a homogeneous and viscous solution was obtained. 600.0 µL of PEG200 was then added to the solution under stirring. The solution was again stirred with a magnetic bar until a homogeneous but slightly opalescent solution was obtained. 250.0 µL of sterile water for injection was then added to the opalescent solution, which was mixed with a vortex to obtain a homogeneous solution. The formulation was used in the assays below to evaluate the biological properties of Compound 1.

Figure 1A:
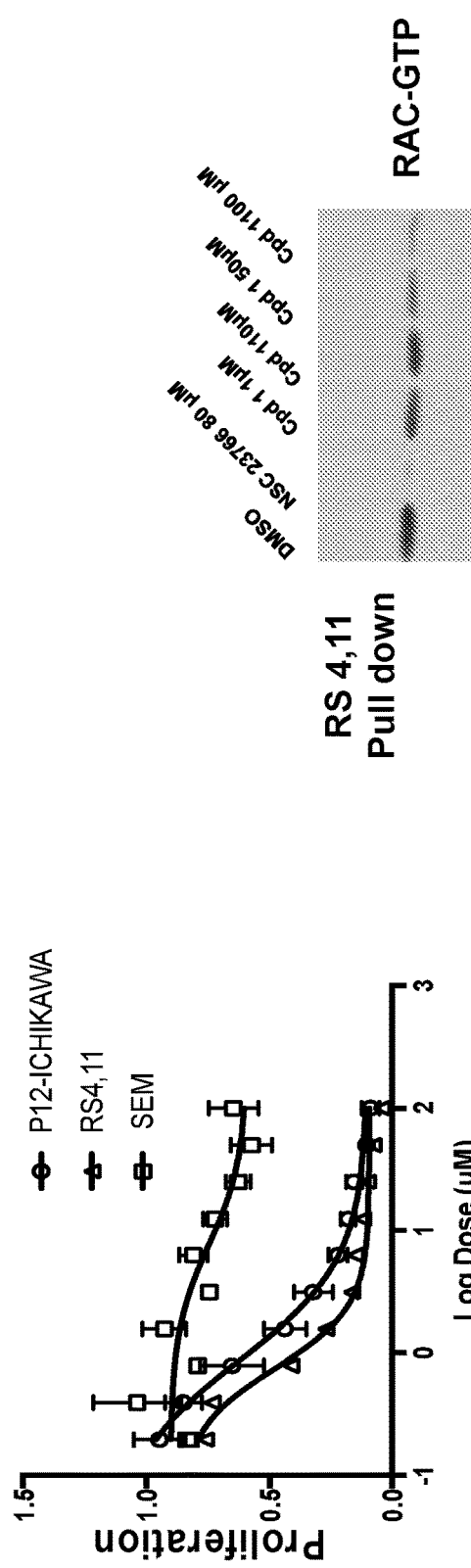
FIG. 1(a) shows dose dependent response curves of Compound 1 in inhibiting proliferation of SEM, RS4,11, and P12 cell lines.

Compound 1 was assayed for inhibition of proliferation in three leukemia cell lines, i.e., (1) SEM, (2) RS4,11, and (3) P12 by ICHIKAWA. The cells for the proliferation assay were spun down and re-suspended. The cell suspension was then divided and Compound 1 was added in desired concentrations and subsequently plated. Following an incubation period, the Cell Titer Glo reagent (Promega CellTiter 96® Aqueous Non-Radioactive Cell Proliferation Assay) was added and allowed to incubate. The absorbance is subsequently measured at 490 nm using a plate reader. The does dependent response curves using serial dilutions of Compound 1 are shown in FIG. 1(a). The results show that IC50 values of Compound 1 ranged between 0.8 and 7 µM.

Figure 1B:
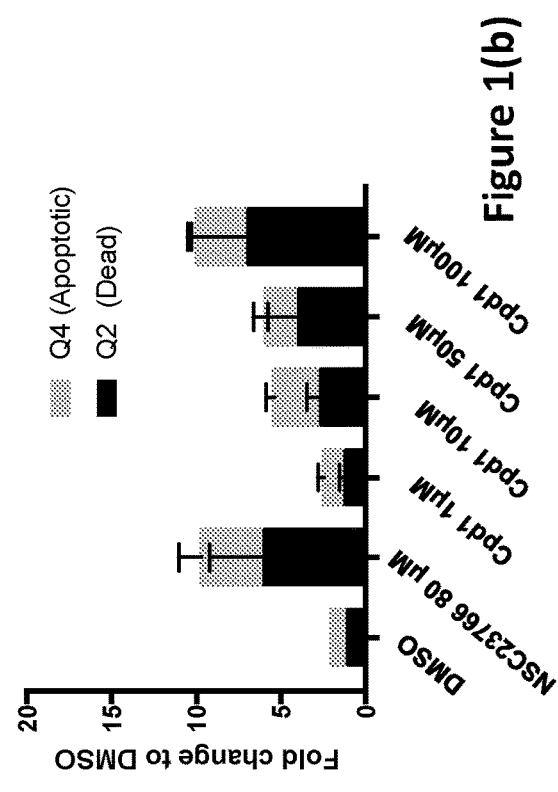
FIG. 1(b) shows a Western Blot analysis indicating that Compound 1 resulted in dose dependent reduction of Rac activation, but had no significant effect on total Rac levels.

Compound 1 was further analyzed for its effect on cell apoptosis and cell death using a flow based assay using Annexin V kit. The results are shown in FIG. 1(b), which shows the effect of DMSO as a vehicle, NSC23766 as a reference compound, and Compound 1 on apoptosis and cell death in the SEM cell line. As shown in FIG. 1(b), Compound 1 caused cells apoptosis and cell death in the SEM cell line in a dose-dependent manner.

Further, a biochemical pull down assay using the SEM cell line was performed to confirm specific inhibition of Rac activation by Compound 1 as indicated by disruption of the interaction between Rac and GTPase. The assay initially required treatment of cells followed by pull down and analysis with Western blot. The cells were first starved in serum free media for 2 hours. They were then re-suspended in serum-containing medium. NSC23766 and Compound 1 were added at desired concentrations. Following incubation for the desired length of time, the cells were pelleted and lysed with Magnesium Lysis Buffer (Millipore $Mg^{2+}$ lysis/wash buffer). The Rac protein and any bound proteins were then collected with Pak Beads (Millipore Rac/CDC42 Assay Reagent (PAK-1 PBD, agarose). Bound protein was subsequently removed with elution buffer and subject to Western Blot analysis. FIG. 1(c) shows a Western Blot analysis indicating that Compound 1 resulted in a significant reduction of Rac activation, but had no significant effect on total Rac levels.

Example 3: Evaluation of Compound 1 for its Toxicity

Figure 2:
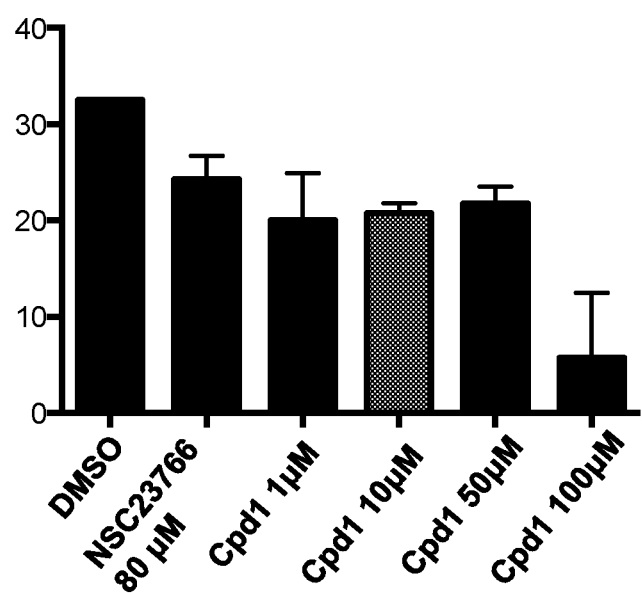
FIG. 2 shows the toxicity test results of DMSO, NSC23766, and Compound 1 in a colony forming unit assay.

The formulation obtained in Example 2 was used for evaluating the toxicity of Compound 1 in a colony forming unit assay (CFU assay), which was performed by plating mononuclear bone marrow cells from WT mice in methylcellulose media supplemented with different doses of Compound 1, NSC23766, and DMSO. The number of colonies formed in each condition was scored 7 days after plating. The test results are shown in FIG. 2. As shown in FIG. 2, Compound 1 did not exhibit toxicity toward clonogenic progenitor bone marrow cells until a concentration >100 fold the IC:50 (~100 micromolar) was utilized.

Example 4: In Vivo Assay for Evaluating Pharmacokinetics of Compound 1

The formulation obtained in Example 2 was assayed to evaluate the pharmacokinetics of Compound 1 in mice. Mice were administered with Compound 1 by oral gavage and then the plasma was collected at the indicated time points to determine the concentration of the compound remaining in the plasma.

Figure 3:
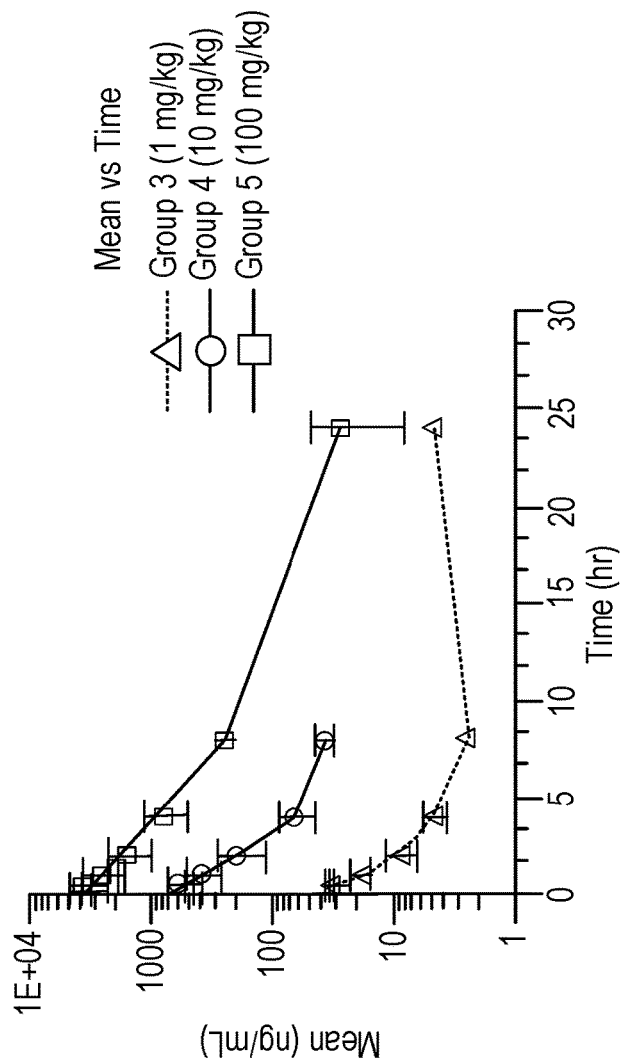
FIG. 3 shows mean maximum plasma concentration of compound 1 following oral administration to male C57Bl/6J mice at different dosages.

Mean plasma concentrations of Compound 1 were recorded over time after oral administration of the indicated doses of Compound 1 (i.e., 1, 10 and 100 mg/kilogram of body weight). The results are shown in FIG. 3. The table in FIG. 3 indicates the mean maximum concentration (Cmax) and the time to reach maximum concentration (Tmax) for Compound 1 at the indicated doses.

Example 5: In Vivo Assay for Evaluating Anti-Leukemia Activities of Compound 1

Bioluminecence imaging (BLI) analysis was performed by treating a mouse model (8 mice) of human leukemia (P12 xenograft) with two different doses of Compound 1 (i.e., 10 and 100 mg/kilogram of body weight) using the formulation obtained in Example 2. P12 cells were transduced with a vector encoding for Luciferase and mCherry as a fluorescent marker. Treatment was started 5 days after inoculation of the cell line, and carried out by oral gavage for 18 days twice a day. Mice were imaged twice a week to obtain a quantification of the disease burden.

Figure 4A:
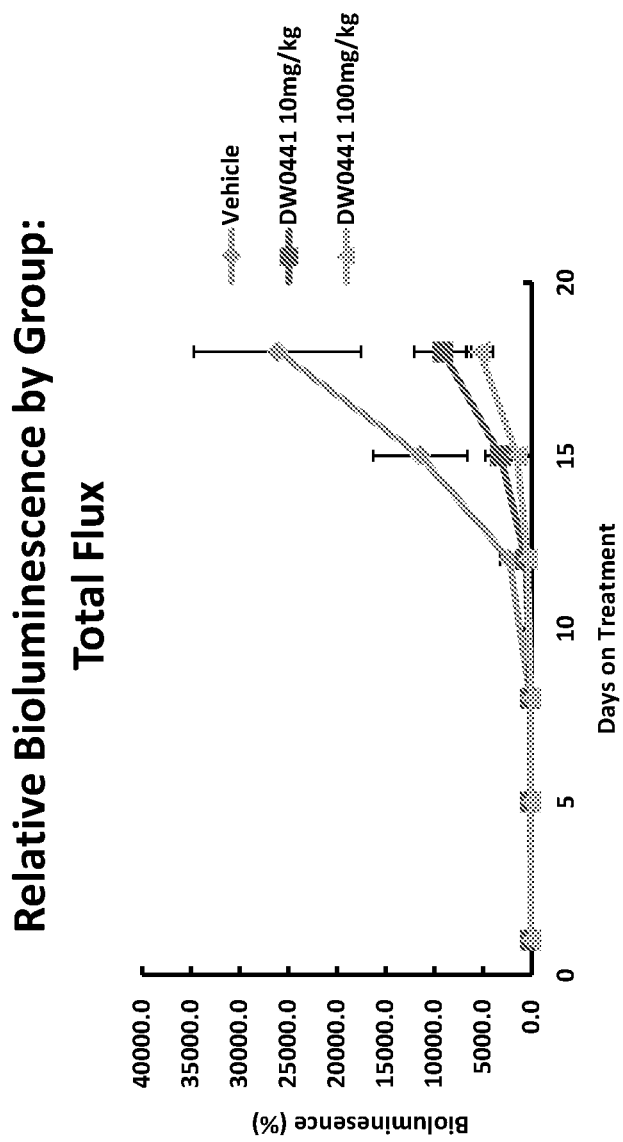
FIG. 4(a) shows the bioluminescence data obtained from the mice treated with a vehicle and Compound 1 at 10 mg/kg and 100 mg/kg. Error bars represent standard error of the mean.
Figure 4B:
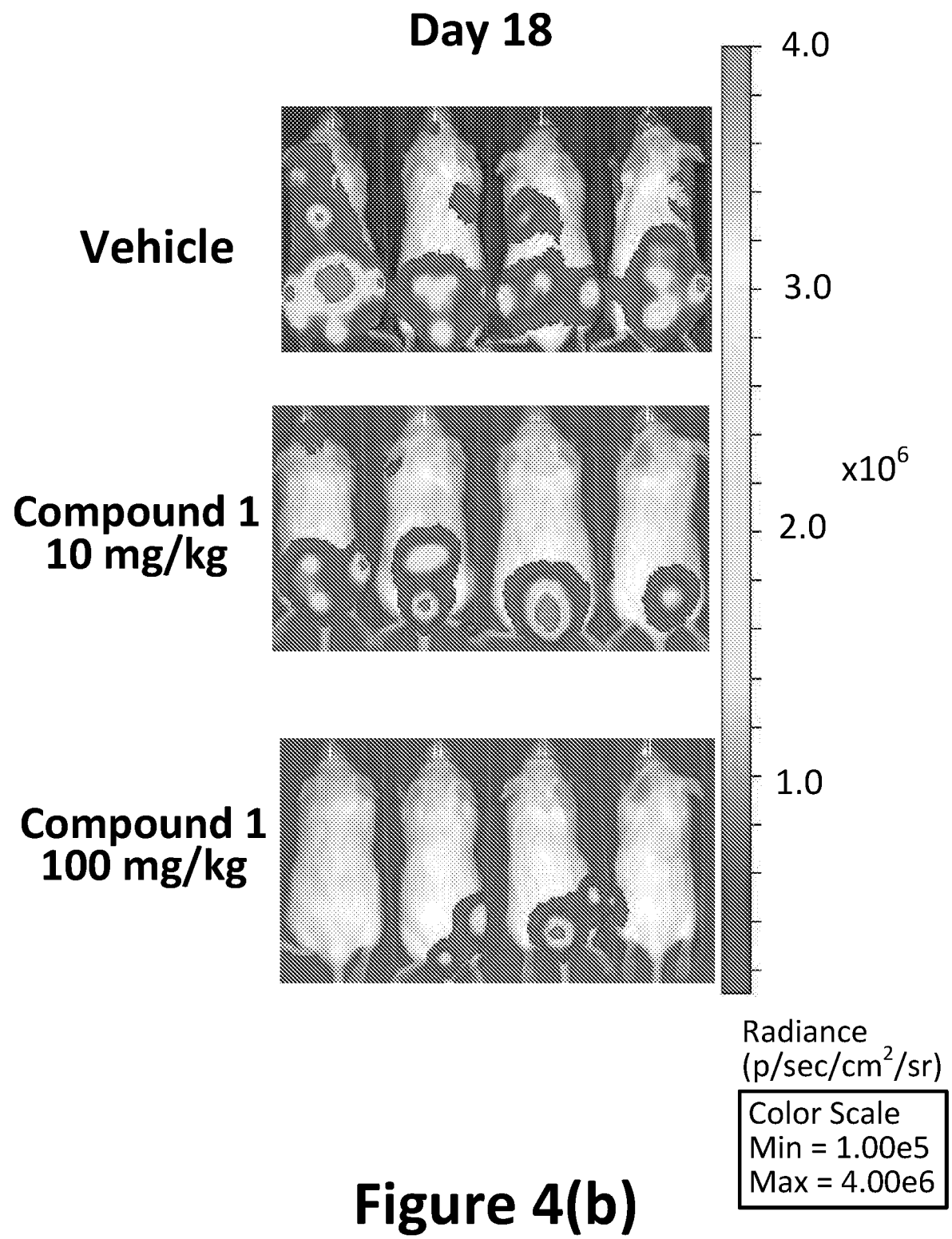
FIG. 4(b) shows representative actual images obtained after mice in the groups treated with a vehicle and Compound 1 for 18 days.

The results were shown in FIGS. 4(a)-6. Specifically, FIG. 4a shows the bioluminescence data obtained from the mice treated with Compound 1 and a vehicle. As shown in this figure, Compound 1 significantly reduced the bioluminescence in the mice at 10 mg/kg and 100 mg/kg, suggesting that this compound effectively inhibited leukemia proliferation. FIG. 4(b) shows representative actual images obtained after mice in the groups treated with Compound 1 and a vehicle for 18 days.

Figure 5:
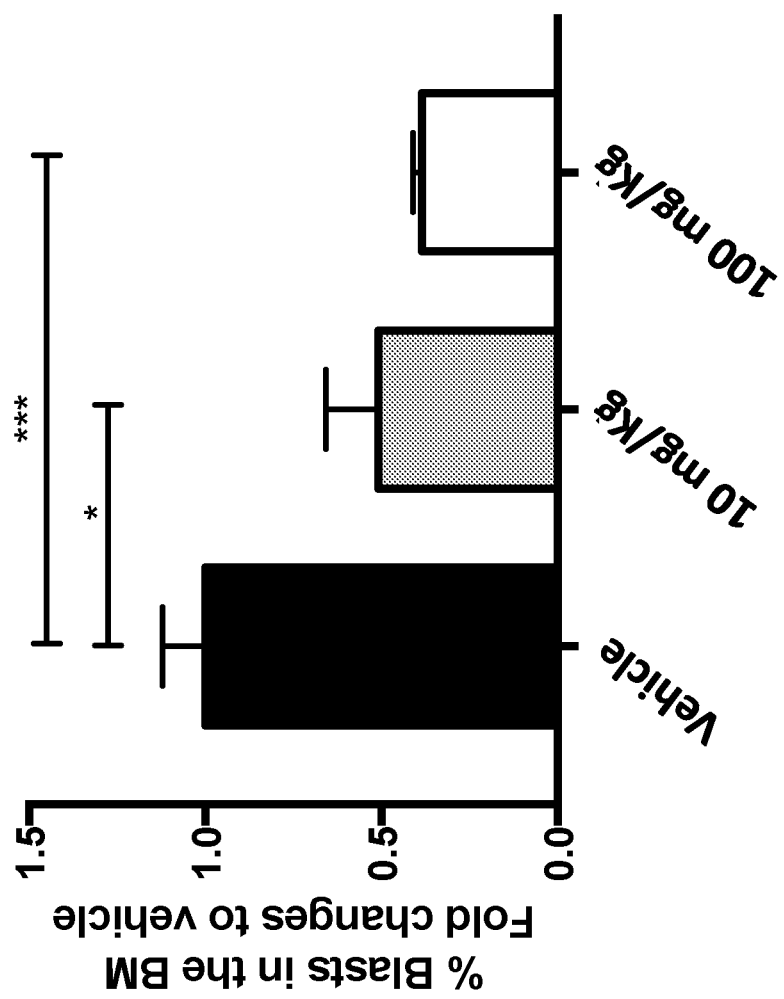
FIG. 5 shows the percentage of mCherry positive cells in the bone marrow of mice treated with a vehicle and Compound 1 at 10 mg/kg and 100 mg/kg. Error bars represent standard error of the mean.

FIG. 5 shows the percentage of mCherry positive cells in the bone marrow of mice from the three cohorts of the above efficacy study using the vehicle and Compound 1. Data is expressed as fold change to the vehicle group. As shown in FIG. 5, Compound 1 was able to effectively inhibit proliferation the cancel cell at dosages of 10 mg/kg and 100 mg/kg.

Figure 6:
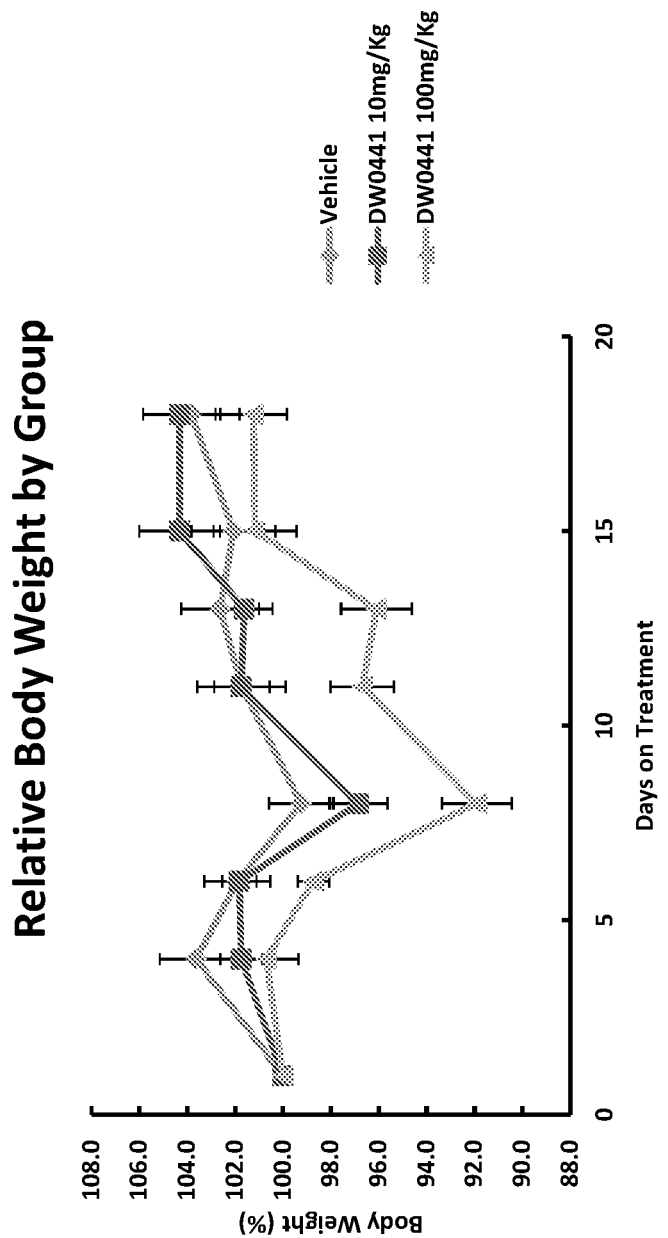
FIG. 6 shows the relative weight of the mice in the three groups treated with the vehicle and Compound 1 at 10 mg/kg and 100 mg/kg. Error bars represent standard error of the mean.

Further, FIG. 6 shows the relative weight of the mice in the three groups treated with the vehicle and Compound 1. As shown in FIG. 6, the weights of the mice in these three groups (i.e., each of which is based on the average weight of the mice in each group and normalized to the average weight before treatment) are relatively stable over the course of treatment, suggesting that Compound 1 exhibited no or low toxicity.

Example 6: Determining Binding Target of Compound 5

Compound 5 (also referred to as DW0254) showed dose-dependent inhibition of Rac activation and induced apoptosis in sensitive leukemic cell lines. Prior work using 2D NMR and HTRF binding assays demonstrated that no binding of Compound 5 to Rac or displacement of Tiam1 (a Rac GEF) binding to Rac.

To determine its target, Compound 5 was investigated using photoaffinity labeling mass spectrometry (PALMS). After demonstrating that the labeled molecule retained function, cells were incubated with the photoaffinity probe and crosslinked with UV-radiation to generate a covalent bond between the probe and putative target proteins.

Subsequent mass spectrometry analysis identified PDE6D as a target protein. The interaction was validated using three independent biophysical methods: Microscale Thermophoresis, Thermal shift and Surface plasmon resonance.

PDE6D is the delta subunit for the rod-specific photoreceptor phosphodiesterase, a key enzyme in phototransduction cascade. PDE6D interacts with a number of prenylated G proteins of the RAS superfamily. PDE6D appeared to act as chaperone for RAS between membranes. Further analysis confirmed that Compound 5 inhibited RAS activation in several RAS mutated leukemia cell lines at concentrations similar to the inhibition of Rac. In addition, Compound 5 inhibited the interaction of PDE6D with RAS and ARL2/3, another known interacting protein of PDE6D. Thus, Compound 5 appeared to affect the PDE6D/ARL-dependent trafficking of RAS. RAS transformation in some experimental models has been shown to be dependent on Rac, so these studies suggest the effect of Compound 5 on Rac activation may be due to inhibition of RAS.

In addition, experimental results showed that Compound 5 bound to PDE6D, and affected PDE6D/ARL2/3-dependent trafficking of RAS in P12 cells (i.e., human T cell leukemia cell line) with NRAS$^{G12D}$ mutation. On the other hand, experimental results showed that PDE6D is not critical for the survival of SEM cells (i.e., human B acute lymphoblastic leukemia cell line), and may not be the binding target of DW0254 in SEM cells.

Septins are GTP binding proteins and were originally identified as proteins required for cytokinesis in yeast cells. The 13 mammalian septins identified so far are called SEPT1-SEPT12 and SEPT14. SEPT11 has been first described as a component of septin complexes in brain tissues. Previous studies have shown the role of SEPT11 in the cytoarchitecture of neurons and in GABAergic synaptic connectivity. SEPT11 and other four septin genes (SEPT2, SEPT5, SEPT6, and SEPT9) have been identified as MLL fusion partners, suggesting a role of SEPT11 in MLL-rearranged leukemia.

Experimental results showed that the removal of the SEPT11 gene in P12 cells did not change the cell growth and its response to Compound 5. On the other hand, experimental results showed that the SEPT11 protein deficient SEM cells showed polyploidy phenotype, decreased cell growth, and decreased IC$_{50}$ compared to wild type SEM cells when treated with Compound 5. In addition, long term treatment of Compound 5 in SEM cells led to the aneuploidy phenotype.

Other embodiments are within the scope of the following claims.

What is claimed is:

1. A compound of formula (I) or a salt thereof:

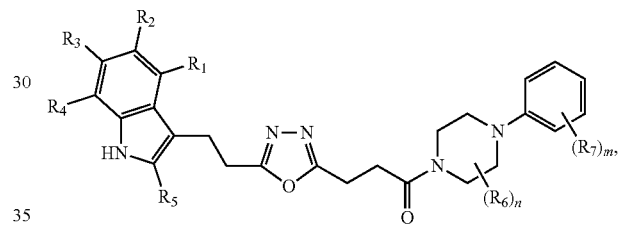

wherein
n is 0, 1, 2, 3, or 4;
m is 0, 1, 2, 3, or 4;
each of $R_1$, $R_2$, $R_3$, $R_4$, and $R_5$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$;
each of $R_6$, independently, is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$;
each of $R_7$, independently, is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $SR_a$, $COOR_a$, $OC(O)R_a$, $C(O)R_a$, $C(O)NR_aR_b$, $S(O)_2NR_aR_b$, or $NR_aR_b$;
each $R_a$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and
each $R_b$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

2. The compound of claim 1, wherein n is 0.
3. The compound of claim 1, wherein m is 1.
4. The compound of claim 1, wherein $R_7$ is halo.

5. The compound of claim 1, wherein $R_7$ is F.

6. The compound of claim 1, wherein R7 is F at the para position.

7. The compound of claim 1, wherein each of $R_1$, $R_2$, $R_3$, $R_4$, and $R_5$ is H.

8. The compound of claim 1, wherein the compound is

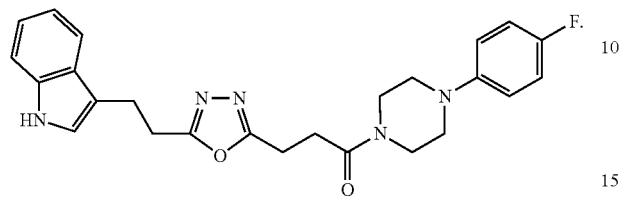

9. A pharmaceutical composition, comprising the compound of claim 1 and a pharmaceutically acceptable carrier.

10. A method of treating a Rac-GTPase mediated disorder in a subject, comprising administering to the subject in need thereof an effective amount of the compound of claim 1;
    wherein the Rac-GTPase mediated disorder is leukemia and the method ameliorates or relieves a symptom of leukemia.

11. The method of claim 10, wherein cancer is pediatric acute lymphocytic leukemia.

12. A method of inhibiting Rac activity in a cell, comprising contacting the cell with an effective amount of the compound of claim 1.

* * * * *